United States Patent
Chen et al.

(10) Patent No.: US 10,002,741 B2
(45) Date of Patent: Jun. 19, 2018

(54) ELECTRON MICROSCOPE WITH PLURAL X-RAY DETECTORS FOR ACQUIRING ELEMENTAL SPECTRUM

(71) Applicant: Industrial Technology Research Institute, Hsinchu (TW)

(72) Inventors: Fu-Rong Chen, Hsinchu (TW); Tsu-Wei Huang, Taoyuan County (TW); Chin-Liang Hsu, Pingtung County (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 376 days.

(21) Appl. No.: 14/583,403

(22) Filed: Dec. 26, 2014

(65) Prior Publication Data

US 2016/0163503 A1 Jun. 9, 2016

(30) Foreign Application Priority Data

Dec. 9, 2014 (TW) .............................. 103142736 A

(51) Int. Cl.
*H01J 37/28* (2006.01)
*H01J 37/244* (2006.01)
*G01N 23/225* (2018.01)

(52) U.S. Cl.
CPC ........ *H01J 37/244* (2013.01); *G01N 23/2252* (2013.01); *H01J 37/28* (2013.01);
(Continued)

(58) Field of Classification Search
CPC ............. H01J 37/244; H01J 2237/2442; H01J 2237/2807; H01J 2237/2561;
(Continued)

(56) References Cited

U.S. PATENT DOCUMENTS

| 2008/0142706 A1* | 6/2008 | Michelmann | H01J 49/423 250/292 |
| 2009/0033913 A1* | 2/2009 | Mott | G01R 29/02 356/51 |

(Continued)

OTHER PUBLICATIONS

Watanabe, Ackland and Williams (1999), The effect of large solid angles of collection on quantitative X-ray microanalysis in the AEM. Journal of Microscopy, 195: 34-43. doi:10.1046/j.1365-2818. 1999.00481.*

(Continued)

*Primary Examiner* — Brooke Purinton
(74) *Attorney, Agent, or Firm* — WPAT, PC

(57) ABSTRACT

An electron microscope includes a stage, a charged particle beam generator, a plurality of elemental spectrum detectors and a reader. The stage is configured for carrying a sample. The charged particle beam generator is configured for generating a charged particle beam to bombard the sample. The elemental spectrum detectors is configured for detecting X ray emitted from the sample being bombarded by the charged particle beam and outputting a plurality of corresponding spectrum detecting signals. The reader is configured for calibrating a plurality of counting signals generated by the spectrum detecting signals and summing the calibrated counting signals to obtain an elemental spectrum of the sample. The collection time of elemental spectrum of the above-mentioned electron microscope can be shortened. A reader and an acquiring elemental spectrum method applied to the above-mentioned electron microscope are also disclosed.

17 Claims, 5 Drawing Sheets

(52) U.S. Cl.
CPC . *H01J 2237/226* (2013.01); *H01J 2237/2445* (2013.01); *H01J 2237/24495* (2013.01); *H01J 2237/24585* (2013.01); *H01J 2237/2555* (2013.01)

(58) Field of Classification Search
CPC ... H01J 2237/24495; H01J 2237/24465; H01J 2237/2446
See application file for complete search history.

(56) References Cited

U.S. PATENT DOCUMENTS

| | | | |
|---|---|---|---|
| 2011/0204229 A1* | 8/2011 | Schamber | H01J 37/244 250/311 |
| 2012/0160999 A1* | 6/2012 | Zaluzec | H01J 37/244 250/307 |
| 2014/0070095 A1* | 3/2014 | Schoenmakers | G01N 23/046 250/305 |

OTHER PUBLICATIONS

Moran, K. & Wuhrer, R. Microchim Acta, "Quantitative Bulk and Trace Element X-Ray Mapping Using Multiple Detectors" (Apr. 18, 2006) vol. 155: Issue 1-2; pp. 59-66.*

* cited by examiner

ELECTRON MICROSCOPE WITH PLURAL X-RAY DETECTORS FOR ACQUIRING ELEMENTAL SPECTRUM

BACKGROUND OF THE INVENTION

1. Field of the Invention

The present invention relates to an electron microscope and a method for acquiring an elemental spectrum, and particularly to an electron microscope having a plurality of elemental spectrum detectors and a method for acquiring an elemental spectrum.

2. Description of the Prior Art

Energy dispersive X-ray Analytics (EDS) is a technology that acquires a characteristic X-rays spectrum induced by bombarding a sample with a charged particle beam (such as e-beam (electron-beam)) to analyze the energy positions of each peak value, so that a composition of the sample excited by a charged particle beam can be recognized and the proportion of each element can further be quantitatively calculated as well. Therefore, the Energy dispersive X-ray Analytics technology has been widely applied in the material analysis methods of various industries. However, the X-ray signal emitted from the sample bombarded with electrons may be extremely weak and may be influenced by solid angle, i.e. the relative geometrical configuration between the detector and the sample. As a result, collecting an elemental spectrum may be quite time-consuming resulted in very expensive time cost.

To sum up the foregoing descriptions, it is a very important goal for now to effectively acquire the X-rays signal emitted from the sample bombarded with electrons to shorten the collecting time of an elemental spectrum.

SUMMARY OF THE INVENTION

The present invention is directed to an electron microscope and a method for acquiring an elemental spectrum, in which a plurality of elemental spectrum detectors are disposed, and the signals detected by the plurality of elemental spectrum detectors are calibrated and then summed, so as to shorten the collecting time of an elemental spectrum.

An electron microscope of one embodiment of the present invention comprises a stage, a charged particle beam generator, a plurality of elemental spectrum detectors and a reader. The stage is configured for carrying a sample. The charged particle beam generator is configured for generating a charged particle beam to bombard the sample. The plurality of elemental spectrum detectors are configured for detecting the X ray emitted from the sample being bombarded by the charged particle beam and outputting a plurality of corresponding spectrum detecting signals, wherein solid angles of the plurality of elemental spectrum detectors with respect to the sample are different. The reader is configured for calibrating a plurality of counting signals generated based on the spectrum detecting signals and summing the calibrated counting signals to obtain an elemental spectrum of the sample.

A reader of another embodiment of the present invention is in conjunction with an electron microscope to obtain an elemental spectrum, wherein the electron microscope comprises a plurality of elemental spectrum detectors and a plurality of pulse processors. The reader comprises a plurality of first connection ports, a main processing unit, a secondary processing unit and a storage unit. The plurality of first connection ports are respectively electrically connected with the plurality of pulse processors, wherein the plurality of pulse processors are respectively electrically connected with the plurality of elemental spectrum detectors to process the plurality of spectrum detecting signals output by the plurality of elemental spectrum detectors and output a plurality of corresponding counting signals, wherein solid angles of the plurality of elemental spectrum detectors with respect to the sample are different. The main processing unit is electrically connected with the plurality of first connection ports to generate a control instruction and output the control instruction to the plurality of pulse processors. The secondary processing unit is electrically connected with the plurality of first connection ports to receive, calibrate and sum the plurality of counting signals and output the elemental spectrum. The storage unit is electrically connected with the secondary processing unit to store the elemental spectrum.

A method for acquiring an elemental spectrum of yet one embodiment of the present invention comprises: bombarding a sample with a charged particle beam; detecting, with a plurality of elemental spectrum detectors, the X ray emitted from the sample being bombarded by the charged particle beam to generate a plurality of corresponding spectrum detecting signals, wherein solid angles of the plurality of elemental spectrum detectors with respect to the sample are different; and calibrating a plurality of counting signals generated based on the plurality of spectrum detecting signals and summing the calibrated counting signals to obtain an elemental spectrum of the sample.

DESCRIPTION OF THE PREFERRED EMBODIMENT

Figure 1:
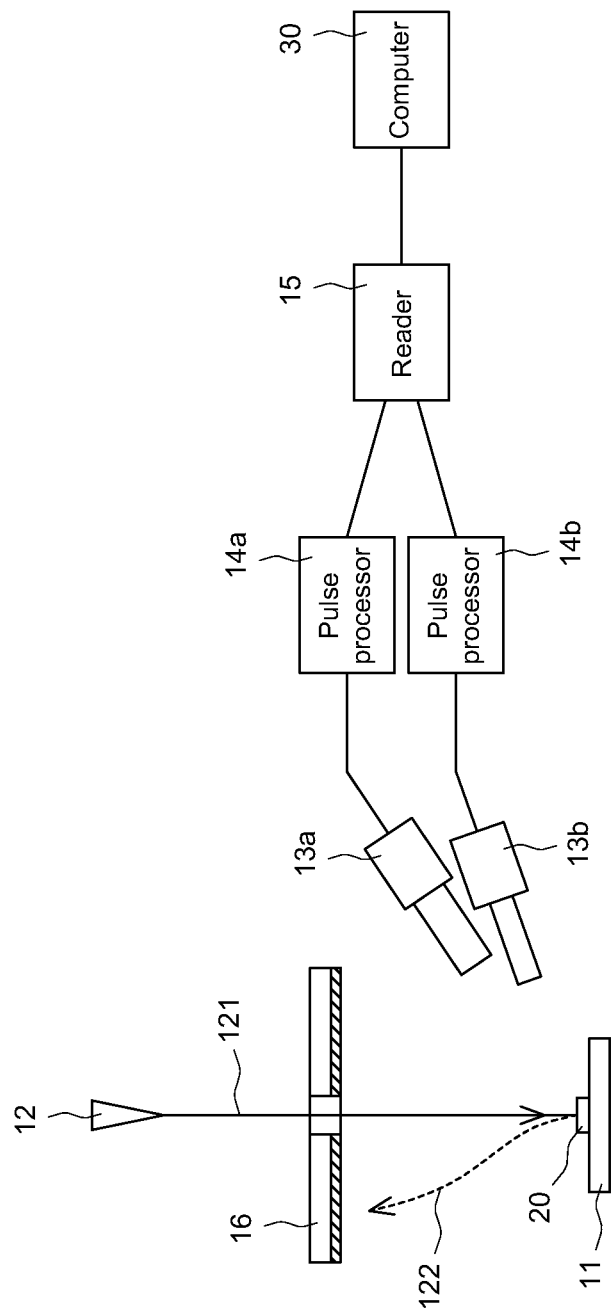
FIG. 1 is a schematic view showing an electron microscope of one embodiment of the present invention.

Various embodiments of the present invention will be described in detail below and illustrated in conjunction with the accompanying drawings. In addition to these detailed descriptions, the present invention can be widely implemented in other embodiments, and apparent alternations, modifications and equivalent changes of any mentioned embodiments are all included within the scope of the present invention and based on the scope of the Claims. In the descriptions of the specification, in order to make readers have a more complete understanding about the present invention, many specific details are provided; however, the present invention may be implemented without parts of or all the specific details. In addition, the well-known steps or elements are not described in detail, in order to avoid unnecessary limitations to the present invention. Same or similar elements in Figures will be indicated by same or similar reference numbers. It is noted that the Figures are schematic and may not represent the actual size or number of the elements. For clearness of the Figures, some details may not be fully depicted.

It is needed to describe in advance that, a term "electron microscope" mentioned herein refers not only to a device in which a sample is bombarded with an electron beam and detect related signals for imaging, but also to a device in which a sample is bombarded with other charged particle beams, e.g., positrons or other charged ions, and detect related signals for imaging. Please refer to FIG. 1, an electron microscope of one embodiment of the present invention comprises a stage 11, a charged particle beam generator 12, a plurality of elemental spectrum detectors 13a, 13b and a reader 15. The stage 11 is configured for carrying a sample 20. For example, the stage 11 comprises appropriate fixing elements to fix the sample. In one embodiment, the stage 11 may also comprise other mechanical members, so that the stage 11 may perform motions such as rotation, tilt or shift, etc. The charged particle beam generator 12 is configured for generating a charged particle beam 121 to bombard the sample 20. In one embodiment, the charged particle beam 121 may be an electron beam, a positron beam or a charged ion beam, etc. It may be understood that the electron microscope of the present invention further comprises prior-art members, such as a focusing device and a chamber for forming a vacuum environment, etc. Other related prior-art members of the electron microscope may be appreciated by those skilled in the art and carried out accordingly, and related descriptions are omitted here.

Continued with the above descriptions, the plurality of elemental spectrum detectors 13a, 13b are configured for detecting the X ray emitted from the sample 20 being bombarded by the charged particle beam 121 and outputting a plurality of corresponding spectrum detecting signals. In one embodiment, the spectrum detecting signals detected by the elemental spectrum detectors 13a, 13b may be amplified with an amplifier, so as to facilitate subsequent signal processing. It may be understood that due to the limitation of the space, solid angles of the elemental spectrum detectors 13a, 13b with respect to the sample 20 may be the same or different. The reader 15 is configured for calibrating a plurality of counting signals generated based on the plurality of spectrum detecting signals and summing the calibrated counting signals to obtain an elemental spectrum of the sample 20. For example, the calibrating method may be a linear calibration. In one embodiment, each elemental spectrum detectors 13a, 13b may be respectively electrically connected with a pulse processor 14a, 14b. The pulse processor 14a, 14b may process the spectrum detecting signals detected by the elemental spectrum detectors 13a, 13b to obtain corresponding counting signals.

The reader 15 may transmit the acquired elemental spectrum to a backend computer 30 to be studied by a user or for other uses. For example, the electron microscope of the present invention comprises a charged particle detector 16, which is configured for detecting back-scattered charged particles 122 or secondary charged particles emitted from the sample 20 being bombarded by the charged particle beam 121 and outputting a corresponding charged particle detecting signal. A corresponding scanning image may be formed based on the charged particle detecting signal detected by the charged particle detector 16. The computer 30 may map the elemental spectrum of the sample 20 to the scanning image of the sample 20. For example, the computer 30 may recognize an elemental composition of the sample in the sample detecting area and/or may further quantitatively calculate the proportion of each element, and may mark the elemental composition and the proportion thereof on the scanning image of the sample. It may be understood that the elemental spectrum acquired by the reader 15 may not be limited to be mapped to a two-dimensional scanning image, and the elemental spectrum may only present an elemental composition and/or a proportion of each element of a single point scanning or line scanning area. It is noted that the reader 15 may be implemented by hardware or software. For example, the reader 15 may be installed in the computer 30 in a form of software, so as to perform processes such as calibration and summation, etc. In order to reduce the computing load of the computer 30, the reader 15 may be implemented by hardware, which detailed architecture will be described later.

Figure 2:
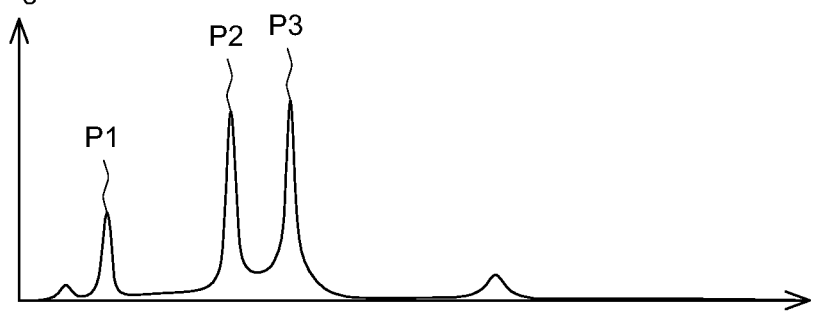
FIG. 2 is a schematic view showing the elemental spectrum detected by different elemental spectrum detectors.
Figure 2:
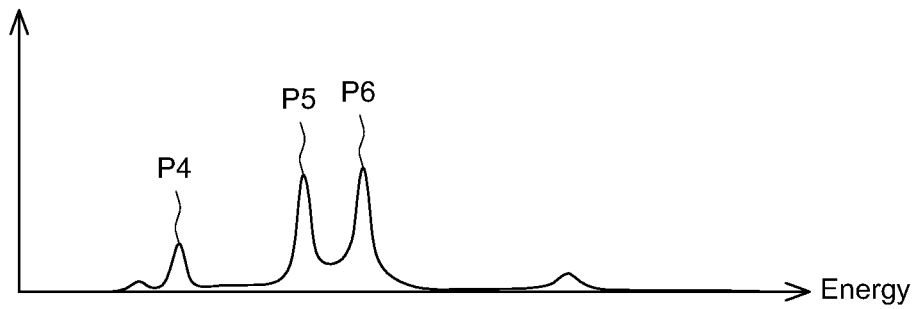

The measurement results measured by the elemental spectrum detectors may be influenced by the solid angle, i.e. the relative geometric configuration between the elemental spectrum detectors and the sample. In other words, a detecting area of the elemental spectrum detector and a distance between the elemental spectrum detector and the sample may both influence the measurement result measured by the elemental spectrum detector. Therefore, under an ideal condition, preferred measurement results may be obtained by selecting the elemental spectrum detectors having the same specification and disposing the elemental spectrum detectors on the same torus (i.e., having the same solid angle). However, the constrained space of the electron microscope (such as a scanning electron microscope) may be limited and a variety of detectors may be included, so that the solid angle between the plurality of elemental spectrum detectors and the sample may be impossibly the same. Therefore, the elemental spectrum detected by the elemental spectrum detectors having different solid angle configurations or specifications may have shift and may not be summed. For example, the elemental spectrum shown in FIG. 2 may be the elemental spectrum detected by the elemental spectrum detectors having different solid angle configurations or specifications, in which the corresponding energy positions of the same element may have shift, wherein the peak P1 should correspond to the peak P4; the peak P2 should correspond to the peak P5; and the peak P3 should correspond to the peak P6. Based on the architecture of the present invention, a peak of the elemental spectrum detected by an elemental spectrum detector 13a having different solid angle configuration or even different specification may be calibrated to a corresponding peak of the elemental spectrum detected by another elemental spectrum detector 13b to be summed together, so that a correct elemental spectrum may be obtained and the collecting time of the elemental spectrum may be effectively shorten.

Figure 3:
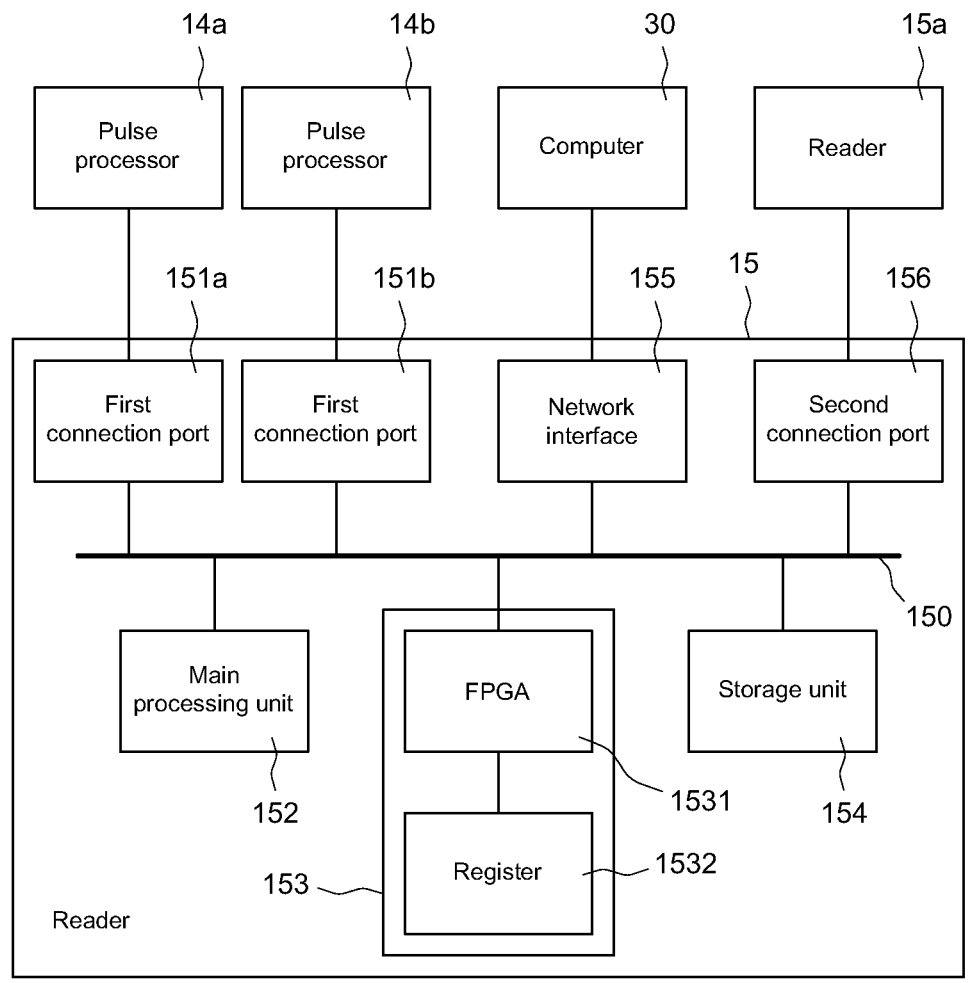
FIG. 3 is a schematic view showing a reader of one embodiment of the present invention.

Please refer to FIG. 3, a reader of one embodiment of the present invention comprises a plurality of first connection ports 151a, 151b, a main processing unit 152, a secondary processing unit 153 and a storage unit 154. In one embodiment, the above-mentioned elements may be electrically connected with each other through a bus 150. The plurality of pulse processors 14a, 14b may be electrically connected with the reader 15 through the first connection ports 151a, 151b respectively to transmit the counting signals to the reader 15. The main processing unit 152 may be electrically connected with the plurality of first connection ports 151a, 151b through the bus 150. The main processing unit 152 may generate a control instruction and output the control instruction to the pulse processors 14a, 14b to control the pulse processors 14a, 14b, e.g., to control the pulse processors 14a, 14b to transmit data to the reader 15. The secondary processing unit 153 may also be electrically connected with the plurality of first connection ports 151a, 151b through the bus 150. The secondary processing unit 153 may be configured to receive the plurality of counting signals from the pulse processors 14a, 14b, and calibrate and sum the plurality of received counting signals to obtain the elemental spectrum. The obtained elemental spectrum may be stored in the storage unit 154 first, and transmitted to the backend computer 30 at the right time. In one embodiment, the secondary processing unit 153 may comprise a Field Programmable Gate Array (FPGA) 1531 and a register 1532. The register 1532 is configured for storing the plurality of received counting signals. In one embodiment, the register 1532 may be a First-In First-Out (FIFO) register. The Field Programmable Gate Array 1531 is electrically connected with the register 1532 to receive, calibrate and sum the plurality of counting signals.

Figure 4:
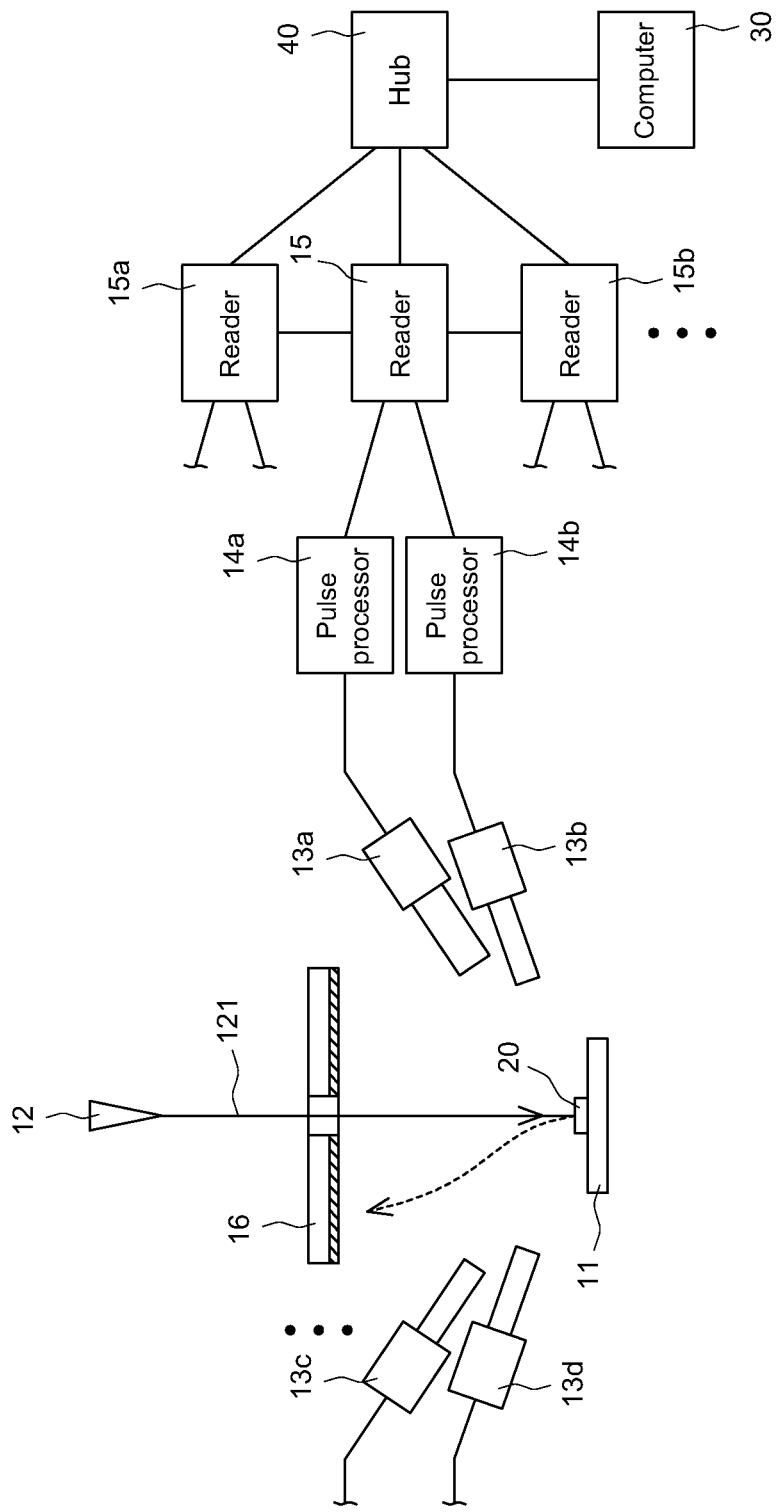
FIG. 4 is a schematic view showing an electron microscope of another embodiment of the present invention.

In one embodiment, the reader 15 of the present invention may be connected with the computer 30 through a network interface 155. Thus, the reader 15 may take advantage of the existing network architecture to transmit the measured elemental spectrum to the computer 30. For example, please refer to FIG. 4, a plurality of readers 15, 15a, 15b may be connected to a hub 40 in the local area network (LAN) through the network interface 155, and when the computer 30 is connected to the hub 40, the elemental spectrum summed by the plurality of readers 15, 15a, 15b may be collected simultaneously by the computer 30. In one embodiment, please refer to FIG. 3 again, the reader 15 comprises a second connection port 156. The reader 15 may be electrically connected with another reader 15a through the second connection port 156 to communicate. Please refer to FIG. 4, for example, the readers 15, 15a may be kept in synchronization via the second connection port 156, so as to facilitate the elemental spectrum measured by the plurality of elemental spectrum detectors 13a, 13b, 13c, 13d connected with the readers 15, 15a to be calibrated and summed. Based on the above architecture, a single computer 30 may be connected with the plurality of readers 15, 15a, 15b simultaneously, and each reader 15, 15a, 15b may operate in synchronization. As such, a number of the elemental spectrum detectors that may be disposed may not be limited.

Figure 5:
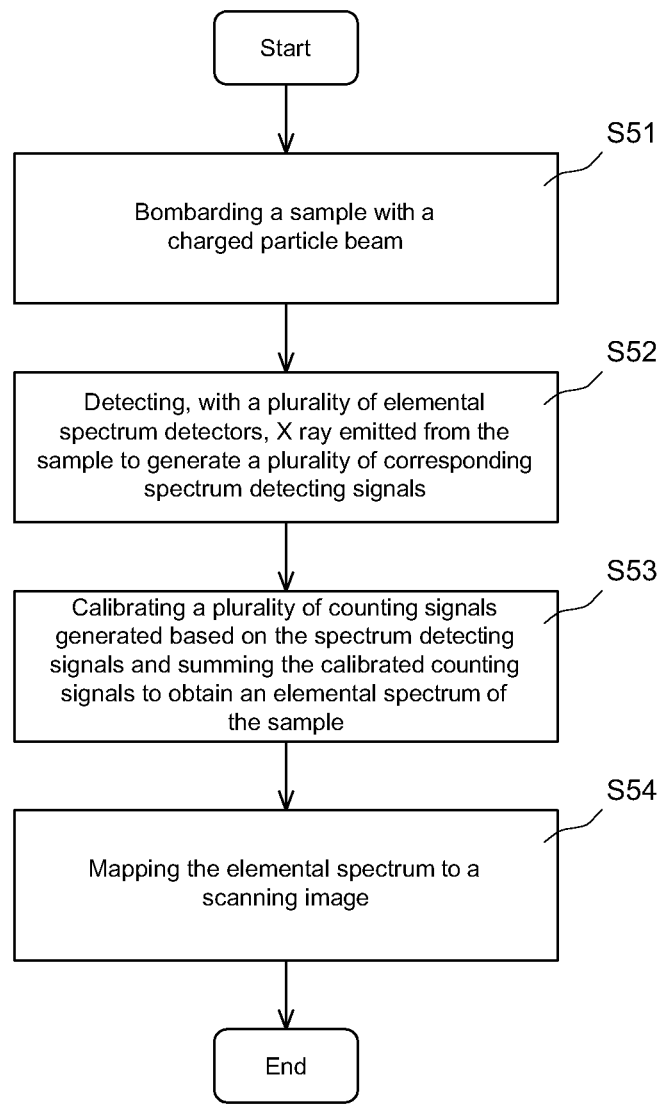
FIG. 5 is a schematic view showing a method for acquiring an elemental spectrum of one embodiment of the present invention.

Please refer to FIG. 1 and FIG. 5, a method for acquiring an elemental spectrum of one embodiment of the present invention is described. First, a sample 20 is bombarded with a charged particle beam 121 (S51). Then, the X ray emitted from the sample 20 being bombarded by the charged particle beam 121 is detected with a plurality of elemental spectrum detectors 13a, 13b to generate a plurality of corresponding spectrum detecting signals (S52). Finally, a plurality of counting signals generated based on the plurality of spectrum detecting signals are calibrated and then summed to obtain an elemental spectrum of the sample 20 (S53). In one embodiment, a method for acquiring an elemental spectrum of the present invention comprises: detecting back-scattered charged particles 122 emitted from the sample 20 being bombarded by the charged particle beam 121 to form a corresponding scanning image. Preferably, the method for acquiring an elemental spectrum of the present invention further comprises: mapping the elemental spectrum obtained in the step S53 to the scanning image (S54). The detailed descriptions of the method for acquiring an elemental spectrum of the present invention are as mentioned above, and are hence omitted here.

To sum up the foregoing descriptions, the electron microscope and the method for acquiring an elemental spectrum of the present invention may be disposed with a plurality of elemental spectrum detectors, and may calibrate the signals detected by the elemental spectrum detectors, so that the signals detected by the elemental spectrum detectors having different solid angle configuration or specification may be summed correctly, so as to greatly shorten the collecting time of an elemental spectrum.

What is claimed is:

1. An electron microscope, comprising:
   a stage configured for carrying a sample;
   a charged particle beam generator configured for generating a charged particle beam to bombard the sample;
   a plurality of elemental spectrum detectors configured for detecting X ray emitted from the sample being bombarded by the charged particle beam and outputting a plurality of corresponding spectrum detecting signals, wherein solid angles of the plurality of elemental spectrum detectors with respect to the sample are different; and
   a reader configured for calibrating a plurality of counting signals generated based on the plurality of spectrum detecting signals and summing the calibrated counting signals to obtain an elemental spectrum of the sample.

2. The electron microscope according to claim 1, further comprising:
   a plurality of pulse processors respectively electrically connected with the plurality of elemental spectrum detectors to process the plurality of spectrum detecting signals and output the plurality of corresponding counting signals.

3. The electron microscope according to claim 2, wherein the reader comprises:
   a plurality of first connection ports respectively electrically connected with the plurality of pulse processors;
   a main processing unit electrically connected with the plurality of first connection ports to generate a control instruction and output the control instruction to the plurality of pulse processors;
   a secondary processing unit electrically connected with the plurality of first connection ports to receive, calibrate and sum the plurality of counting signals and output the elemental spectrum; and
   a storage unit electrically connected with the secondary processing unit to store the elemental spectrum.

4. The electron microscope according to claim 3, wherein the secondary processing unit comprises:
   a register configured for storing the plurality of counting signals; and
   a Field Programmable Gate Array (FPGA) electrically connected with the register to receive, calibrate and sum the plurality of counting signals and output the elemental spectrum.

5. The electron microscope according to claim 3, wherein the reader further comprises:
   a network interface configured for electrically connecting with a computer to transmit the elemental spectrum to the computer.

6. The electron microscope according to claim 3, wherein the reader further comprises:
   a second connection port configured for electrically connecting with another reader, wherein the plurality of readers are connected with each other are kept in synchronization via the second connection port.

7. The electron microscope according to claim 1, further comprising:
   a charged particle detector configured for detecting back-scattered charged particles or secondary charged particles emitted from the sample being bombarded by the charged particle beam and outputting a corresponding charged particle detecting signal, wherein the charged particle detecting signal is configured for forming a corresponding scanning image.

8. The electron microscope according to claim 7, wherein the elemental spectrum is mapped to the scanning image.

9. The electron microscope according to claim 1, being a scanning electron microscope.

10. A reader in conjunction with an electron microscope to obtain an elemental spectrum, the electron microscope comprising a plurality of elemental spectrum detectors and a plurality of pulse processors, the reader comprising:
 a plurality of first connection ports respectively electrically connected with the plurality of pulse processors, wherein the plurality of pulse processors are respectively electrically connected with the plurality of elemental spectrum detectors to process the plurality of spectrum detecting signals output by the plurality of elemental spectrum detectors and output a plurality of corresponding counting signals, wherein solid angles of the plurality of elemental spectrum detectors with respect to the sample are different;
 a main processing unit electrically connected with the plurality of first connection ports to generate a control instruction and output the control instruction to the plurality of pulse processors;
 a secondary processing unit electrically connected with the plurality of first connection ports to receive, calibrate and sum the plurality of counting signals and output the elemental spectrum; and
 a storage unit electrically connected with the secondary processing unit to store the elemental spectrum.

11. The reader according to claim 10, wherein the secondary processing unit comprises:
 a register configured for storing the plurality of counting signals; and
 a Field Programmable Gate Array (FPGA) electrically connected with the register to receive, calibrate and sum the plurality of counting signals and output the elemental spectrum.

12. The reader according to claim 10, further comprising:
 a network interface configured for electrically connecting with a computer to transmit the elemental spectrum to the computer.

13. The reader according to claim 10, further comprising:
 a second connection port configured for electrically connecting with another reader, wherein the plurality of readers are connected with each other are kept in synchronization via the second connection port.

14. A method for acquiring an elemental spectrum, comprising:
 bombarding a sample with a charged particle beam;
 detecting, with a plurality of elemental spectrum detectors, X ray emitted from the sample being bombarded by the charged particle beam to generate a plurality of corresponding spectrum detecting signals, wherein solid angles of the plurality of elemental spectrum detectors with respect to the sample are different; and
 calibrating a plurality of counting signals generated based on the plurality of spectrum detecting signals and summing the calibrated counting signals to obtain an elemental spectrum of the sample.

15. The method for acquiring an elemental spectrum according to claim 14, further comprising:
 processing, with a plurality of pulse processors, the plurality of spectrum detecting signals to generate the plurality of corresponding counting signals.

16. The method for acquiring an elemental spectrum according to claim 14, further comprising:
 detecting back-scattered charged particles or secondary charged particles emitted from the sample being bombarded by the charged particle beam to form a corresponding scanning image.

17. The method for acquiring an elemental spectrum according to claim 16, further comprising:
 mapping the elemental spectrum to the scanning image.

* * * * *